US010549004B2

(12) United States Patent
Hughes et al.

(10) Patent No.: US 10,549,004 B2
(45) Date of Patent: Feb. 4, 2020

(54) RECIRCULATING INERT GAS PURIFICATION APPARATUS USED WITH GLOVEBOXES, GLOVEBOXES INCORPORATING THE SAME AND METHODS OF USING THE SAME

(71) Applicant: WEMS, INC., Hawthorne, CA (US)

(72) Inventors: Melvin W. Hughes, Rancho Palos Verdes, CA (US); Ronald S. Hood, Hawthorne, CA (US); William Carter Mathews, Torrance, CA (US); Dmitry Vernik, Los Angeles, CA (US)

(73) Assignee: WEMS, INC., Hawthorne, CA (US)

( * ) Notice: Subject to any disclaimer, the term of this patent is extended or adjusted under 35 U.S.C. 154(b) by 594 days.

(21) Appl. No.: 14/315,216

(22) Filed: Jun. 25, 2014

(65) Prior Publication Data

US 2015/0004053 A1  Jan. 1, 2015

Related U.S. Application Data

(60) Provisional application No. 61/841,140, filed on Jun. 28, 2013.

(51) Int. Cl.
*A61L 9/00* (2006.01)
*B01J 8/00* (2006.01)

(52) U.S. Cl.
CPC .............. *A61L 9/00* (2013.01); *B01J 8/008* (2013.01); *B01J 2208/00946* (2013.01)

(58) Field of Classification Search
CPC ............................. A61L 9/00; B01D 53/0415
See application file for complete search history.

(56) References Cited

U.S. PATENT DOCUMENTS

| 5,316,560 A | 5/1994 | Krone-Schmidt et al. |
| 5,492,678 A * | 2/1996 | Ota ..................... B01D 53/32 422/174 |
| 6,250,095 B1 * | 6/2001 | Kametani ............. F24F 3/1423 62/271 |
| 2004/0231828 A1 * | 11/2004 | Dunne ................... F25B 35/04 165/104.12 |
| 2013/0263854 A1 * | 10/2013 | Taylor ............... A61M 16/0066 128/204.23 |

FOREIGN PATENT DOCUMENTS

GB  2 290 044 A  12/1995

OTHER PUBLICATIONS

International Search Report and Written Opinion dated Sep. 11, 2014, for International Application PCT/US2014/044175; 10 pages.

* cited by examiner

*Primary Examiner* — Sean E Conley
(74) *Attorney, Agent, or Firm* — Lewis Roca Rothgerber Christie LLP (57) ABSTRACT

An apparatus that may entirely be contained in a glovebox for the removal of at least one contaminant from an inert atmosphere. The apparatus includes a body, a media in the body for the removal of at least one of the contaminants from the inert atmosphere flowing through the media, a fan for causing the inert atmosphere to flow through the media and body, and a motor for driving the fan. The apparatus may be provided in combination with a glovebox. A method of purification of the inert atmosphere using such an apparatus is also provided.

11 Claims, 6 Drawing Sheets

RECIRCULATING INERT GAS PURIFICATION APPARATUS USED WITH GLOVEBOXES, GLOVEBOXES INCORPORATING THE SAME AND METHODS OF USING THE SAME

CROSS-REFERENCE TO RELATED APPLICATION

This application claims priority to and the benefit of Provisional Application No. 61/841,140, filed on Jun. 28, 2013, the entire disclosure of which is incorporated herein by reference.

BACKGROUND OF THE INVENTION

Figure 1:
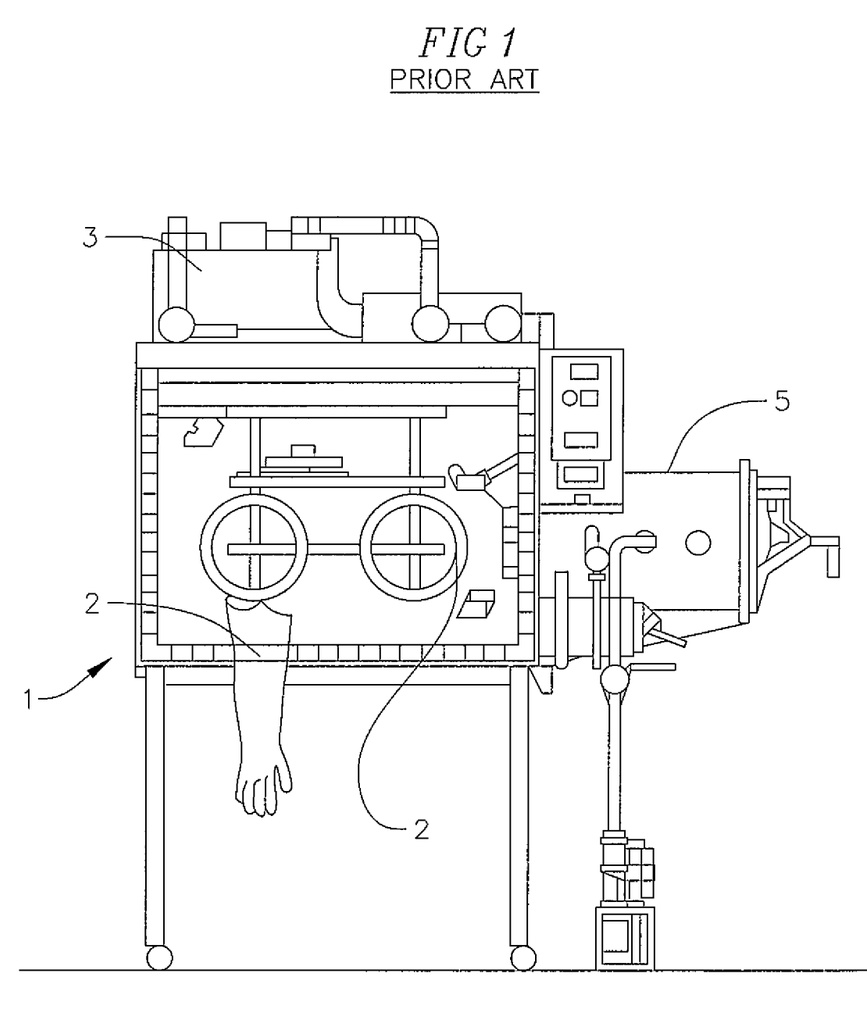
FIG. 1 depicts front and side views of a prior art glovebox.

A glovebox (also known as an inert atmosphere box or containment box) is a hermetically sealed container that is designed to allow one to manipulate objects where a separate inert atmosphere is desired. A typical glovebox 1 is shown in FIG. 1. Built into a side of the glovebox are gloves 2 typically made of an elastic material, arranged in such a way that the user can place their hands into the gloves and perform tasks inside the box without breaking the seal of the container. At least part of the glovebox is transparent to allow the user to see what is being manipulated. A glovebox allows a user to work with substances that must be contained within a very high purity inert atmosphere, such as argon or nitrogen. The inert atmosphere within a glovebox typically needs to be maintained at less than 1 part per million (ppm) moisture, and/or to less than 1 ppm oxygen. To maintain such a low level of moisture, and/or oxygen in the inert atmosphere, media (also referred to herein for convenience as "media", "filtering media" or "removal media") is installed external to the glovebox and inert gas from within the glovebox is circulated through such media. For moisture removal the media used is typically molecular sieves, activated alumina or silica gels and moisture is removed by adsorption. For oxygen removal the media is typically a high surface substrate with a thin layer of surface copper and removes oxygen by the oxidation of the surface copper. The media are housed in a structure, such as a vessel 3, external to the box and conduits 4 are connected to the interior of the box for providing flow of inert gas from the glovebox through the media and back to the glovebox. Moisture removal media and the oxygen removal media may be housed in separate structures or vessels; although more typically they are housed, in layers, in one structure. In either case, the inert gas from the interior of the glovebox is circulated through media containing structure or structures. Examples of gloveboxes are the VAC 101965 OMNI-LAB Glovebox System and the VAC 105320 NEXUS-II Glovebox System available from Vacuum Atmospheres Company. Objects to be worked in the glovebox are placed in the glovebox through an antechamber 5. With time, moisture and oxygen levels in the glovebox increase as the outside atmosphere may permeate through the gloves or enter the glovebox when materials and objects are brought into or removed from the glovebox through the antechamber. The glovebox inert atmosphere is caused to continuously flow from the glovebox through the media and returned to the glovebox for reducing and/or maintaining the inert gas atmosphere moisture and oxygen levels to desirable levels, as for example less than 1 ppm moisture and/or less than 1 ppm oxygen. The glovebox inert gas atmosphere is caused to flow through the media either by a fan assembly located within the glovebox with an outlet port of the fan assembly connected to the conduit 4 connected to the inlet of the vessel containing the media or by a hermetically sealed fan assembly located externally at or near the media vessel 3.

Eventually, the moisture and oxygen removal media in vessel 3 gradually approach their maximum removal capacities and their removal efficiencies decrease until they cannot maintain the desired moisture and/or oxygen level. At that point the removal media needs to be "regenerated." In a typical glovebox system regeneration of the moisture removal media and the oxygen removal media are generally performed at the same time. To accomplish this, flow from the glovebox through the media is stopped. The vessel with the removal media is isolated from the glovebox by closing valves in the conduits connecting the vessel with the glovebox. The vessel containing the oxygen removal media and the moisture removal media is then heated to approximately 200° C. This process takes several hours. Once the desired temperature is reached, an inert gas from a supply tank is connected to the media vessel in a manner that causes flow in the reverse direction to the flow from glovebox inert gas. After the inert regeneration gas passes through the media the gas is vented to the outside or room atmosphere. This regeneration gas purge step typically takes one hour. If the media is for moisture removal, an inert gas with less than 20 ppm moisture is required. If the media is for oxygen removal or both moisture and oxygen removal the inert gas used for regeneration contains 1%-3% hydrogen. Following the purge with the regeneration gas the media is allowed to cool. After cool down, the vessel and removal media are placed under vacuum for several hours. The removal media vessel is then refilled with inert gas to the same pressure as the pressure as that of the glovebox. The isolation valves are then opened and flow of inert gas from the glovebox is reestablished and removal of moisture and/or oxygen from the inert gas may begin.

For a typical glovebox this regeneration process requires 12 to 24 hours. For units with a single vessel of removal media, the glovebox will be out of service for that period of time. If the glovebox has two removal vessels, when the vessel containing the exhausted media is taken off line for regeneration the other vessel, previously regenerated, is placed on-line and will remain on-line until it becomes exhausted and the initial vessel with regenerated media is placed on line.

SUMMARY

In an example embodiment an apparatus is provided for the removal of at least one contaminant from an inert atmosphere. The apparatus includes a body, a media in the body for the removal of at least one of the contaminant from the inert atmosphere flowing through the media, a fan for causing the inert atmosphere to flow through the body and media, and a motor for driving the fan. In another example embodiment, the motor is a brushless motor. In yet another example embodiment, the fan causes the inert atmosphere to flow through the media at least at 5 cubic feet per minute. In a further example embodiment, at least one contaminant is selected from the group consisting essentially of moisture, oxygen, solvent, nitrogen, and combinations thereof. In yet a further example embodiment, the media is selected from the group of media consisting essentially of molecular sieve, activated carbon, silica gel desiccants, copper catalysts and combinations thereof. In another example embodiment, the inert atmosphere is an atmosphere selected from the group consisting essentially of nitrogen, argon, neon, helium, combinations thereof, and air combined with either of the aforementioned atmospheres.

In a further example embodiment, a glovebox with a purification apparatus combination is provided. The combination includes a glovebox having an interior space, a purification apparatus within the interior space for the removal of at least one contaminant from an inert atmosphere within the interior space. The purification apparatus includes a body, a media in the body for the removal of at least one contaminant from the inert atmosphere flowing through the body and media, a fan for causing the inert atmosphere to flow through the media, and a motor for driving the fan. In yet another example embodiment, the motor is a brushless motor. In a further example embodiment, the fan causes the atmosphere to flow through the media at least at 5 cubic feet per minute. In yet a further example embodiment, the combination further includes another purification apparatus. The another purification apparatus includes another body, and another media in the another body for the removal of at least one of the moisture and oxygen from an atmosphere flowing through the another media. The another purification apparatus includes another fan for causing the atmosphere to flow through the another body and the another media, and another motor for driving the another fan. In one example embodiment, another motor is a brushless motor. In another example embodiment, another fan causes air to flow through the another media at least at 5 cubic feet per minute. In a further example embodiment, the media in the purification apparatus body is a media for removing moisture and another media in another purification apparatus body is for removing oxygen. In yet a further example embodiment, at least one contaminant is selected from the group consisting essentially of moisture, oxygen, solvent, nitrogen and combinations thereof. In another example embodiment, the media is selected from the group of media consisting essentially of molecular sieve, activated carbon, silica gel desiccants, copper catalysts and combinations thereof. In yet another example embodiment, the inert atmosphere is an atmosphere selected from the group consisting essentially of nitrogen, argon, neon, helium, combinations thereof, and air combined with either of the aforementioned atmospheres.

In a further example embodiment, a glovebox with a purification apparatus combination is provided. The combination includes a glovebox having an interior space, an apparatus within the interior space for the removal of at least one contaminant from an inert atmosphere within said interior space. The apparatus includes a body, and a media in the body for the removal of at least one contaminant from the inert atmosphere flowing through said media and body. The combination also includes a fan for causing the inert atmosphere to flow through said media, and a motor externally of the glovebox for driving said fan. In yet a further example embodiment, the fan causes the atmosphere to flow through the media at least at 5 cubic feet per minute. In one example embodiment, at least one contaminant is selected from the group consisting essentially of moisture, oxygen, solvent, nitrogen and combinations thereof. In another example embodiment, the media is selected from the group of media consisting essentially of molecular sieve, activated carbon, silica gel desiccants, copper catalysts and combinations thereof. In yet another example embodiment, the inert atmosphere is an atmosphere selected from the group consisting essentially of nitrogen, argon, neon, helium, combinations thereof, and air combined with either of the aforementioned atmospheres. In a further example embodiment the fan is external of the glovebox. In yet a further example embodiment, the fan is internal of the glovebox.

In one example embodiment, a method of removing at least one contaminant from an inert atmosphere within a glovebox is provided. The method includes moving the inert atmosphere through a body within the glovebox, the body including media for the removal of the contaminant. In one example embodiment, moving the atmosphere includes operating a fan located externally of the glovebox for moving the atmosphere. In another example embodiment, moving the atmosphere includes operating a fan located within the glovebox for moving the atmosphere. In yet another example embodiment, the body is coupled to the fan, and the method further includes decoupling the body from the fan; and coupling a new body to the fan including regenerated media. In yet a further example embodiment, the method further includes placing the fan within the glovebox. In yet a further example embodiment, at least one contaminant is selected from the group consisting essentially of moisture, oxygen, solvent, nitrogen and combinations thereof. In one example embodiment, the media is selected from the group of media consisting essentially of molecular sieve, activated carbon, silica gel desiccants, copper catalysts and combinations thereof. In another example embodiment, the inert atmosphere is an atmosphere selected from the group consisting essentially of nitrogen, argon, neon, helium, combinations thereof, and air combined with either of the aforementioned atmospheres.

In a further example embodiment, a filtering capsule is provided. The capsule includes a body having an inlet and an outlet, and a filtering media within the body between the inlet and the outlet for filtering an inert atmosphere in a glovebox that enters the body through the inlet and exits the body through the outlet, wherein the body is coupled to the fan for causing the atmosphere to enter the inlet and exit the outlet. In yet a further example embodiment, the filtering media is selected from the group of filtering media consisting essentially of copper catalysts, molecular sieves, activated carbon, silica gel desiccants and combination thereof.

DETAILED DESCRIPTION

In an embodiment, an apparatus 10 (FIG. 2) for removing moisture and/or oxygen from the environment in a glovebox is provided for use inside a glovebox. For illustrative purposes the apparatus is referred to herein as a "filtering apparatus." The environment in the glovebox is an inert atmosphere. "Inert atmosphere" as used herein means an atmosphere that includes an inert gas as for example argon, neon, nitrogen, helium, and combinations thereof and may include air mixed with such inert gas and inert gas combinations. The filtering apparatus in an example embodiment tends to be small so it does not occupy much of the valued real estate within the glovebox. In an example embodiment, the apparatus has a cylindrical or tubular body 12 having a length 14 of about 7 inches and an inner diameter 16 of about 3 inches and an outer diameter 18 of about 3½ inches. In an example embodiment, the body is made from an acrylic, polycarbonate, PVC, or a metal material. A perforated support member 20, as for example a screen is provided inside the tubular member defining a media support surface. In an example embodiment, the perforated support member is provided closer to a lower end 22 of the body and is resting on a support structure, such as a lip 24 extending internally. The support structure may be integrally formed with the body or may be attached to one interior surface of the body. In an example embodiment, a single annular lip is provided onto which is seated the perforated support member. The perforated support member may be connected or otherwise coupled to an interior surface 26 of the body using other methods. In another embodiment, another support structure may be provided spaced apart from support structure 24 to hold another media. There may also be a perforated support member and support structure on or proximate the opposite end of tubular body 12 and the media may be located between the two perforated support members. The perforated support member has openings or perforations that allow the glovebox inert atmosphere to flow through the removal media. However, such openings or perforations are smaller in diameter than the diameter of the particulates forming a media which will be supported by such member. In one example embodiment media 28 is placed on the perforated support member from the top of the cylindrical body.

Figure 2:
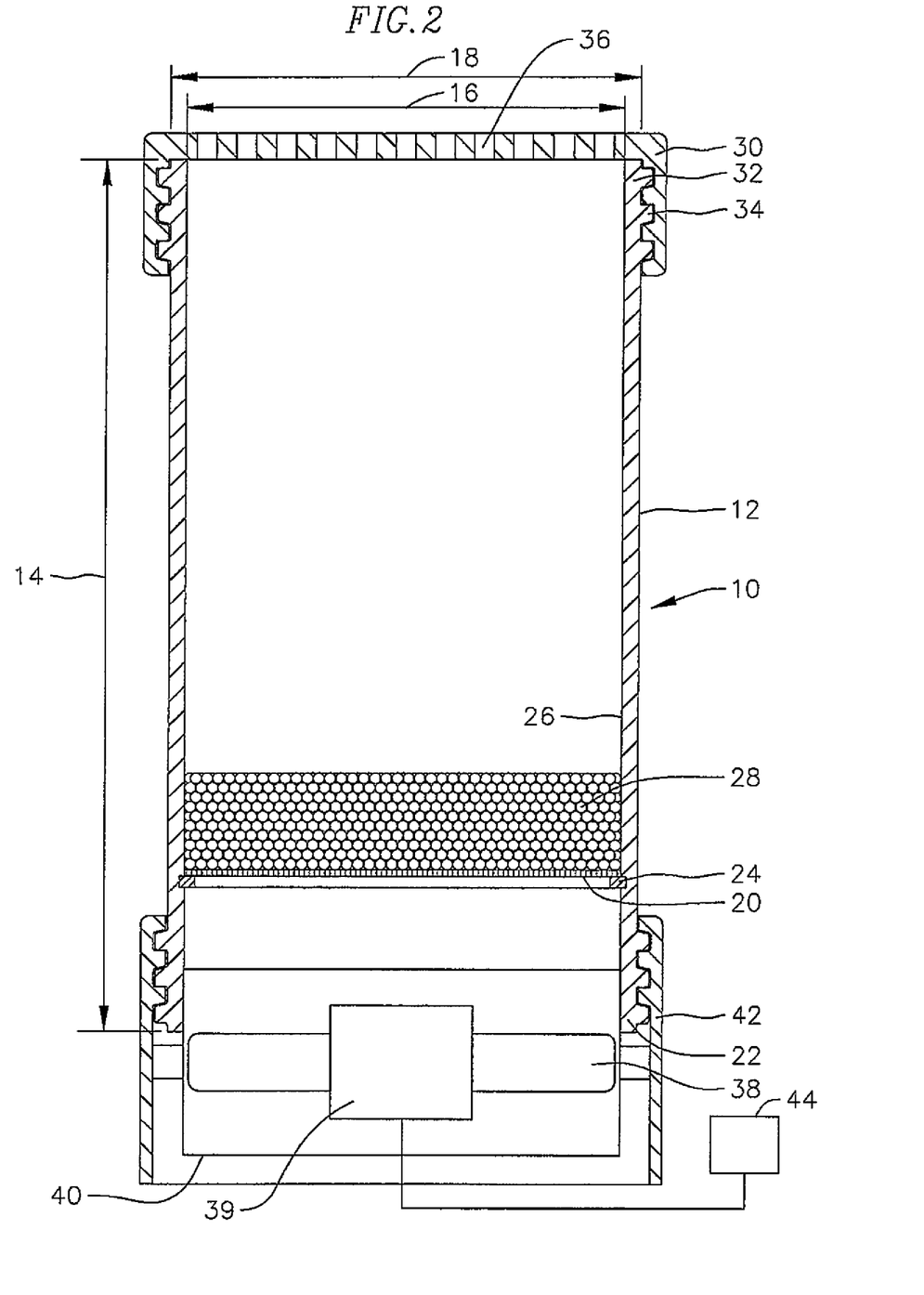
FIG. 2 is a cross-sectional view of an example embodiment apparatus.

A cap 30 may be attached to a top 32 of the cylindrical body 12. For example, the cap may be threaded onto an outer thread 34, formed from an upper end portion of an outer surface of the cylindrical body. The cap has a capping or top surface 36 that is also perforated or may be formed from a screen material as to allow the glovebox inert atmosphere to flow there through.

A fan 38 is placed below the perforated support member 20. In an example embodiment, a fan is driven by a motor 39. In an example embodiment, a motor with fan are provided preassembled as an assembly 40. A motor and fan assembly may be mounted at least partly within the body below the perforated support member 12. In one example embodiment, the fan assembly 40 is mounted within an annular member 42. In an example embodiment, the annular member with the fan assembly is threaded on a lower end of the body as for example shown in FIG. 2. In another example embodiment, the fit between the annular member 42 and the cylindrical body 12 is such that a threaded end of the cylindrical body may just be set in place without engaging the threads. In other embodiments, the fan may be mounted in other locations and may be coupled to the body via a conduit so as that the glovebox inert atmosphere blown by the fan is ducted to the lower perforated support member such that it flows through the media and exits the body through the body upper end. In other example embodiments, the fan may be coupled to an upper end of the body. For example the assembly 40 may be mounted to an upper end of the body or the fan may be coupled to the upper end of the body via a conduit. With either embodiment, the fan causes the inert atmosphere to flow through the body and thus through the filtering media.

In an example embodiment, the motor and fan assembly is capable of providing a flow rate of approximately 5 CFM (cubic feet per minute) through the media at a highest motor speed and about 3 CFM at about half that speed. In an example embodiment, the motor is a brushless motor and runs from power received from power source 44. In an example embodiment, the power source 44 is a 12-volt DC battery. In another example embodiment, the motor is a brushless motor but can run using other types of power sources. Applicant has discovered that a brush motor does not last for more than a few days in the glovebox atmosphere with less than 1 ppm moisture before the brushes are depleted. In an example embodiment, for the motor chosen, the rotational speed is a function of the supplied voltage. In an example embodiment, 12 volts were required for full speed operation of the fan. In an example embodiment, the motor and fan assembly is a PFB 60×60×38 mm series fan assembly. The motor is a brushless motor operating at 12 volts DC. The fan in an example embodiment has a diameter of about 2.36 inches. In addition, Applicant has discovered that small, similarly sized AC motors do not achieve sufficient rotational speeds to provide proper flow rate through the media. This same motor is capable of providing 10 CFM nitrogen through the apparatus when used in an apparatus containing moisture removal media and with the motor running at full speed. At half voltage (i.e., at half speed) the motor will provide a flow about 5 CFM. In other example embodiments, larger fan may be required. In one example having a body having an inner diameter of 3 inches, and about 9.5 inches of filtering media (e.g., moisture removing media and/or oxygen removing media), the fan provided for a maximum flow rate of 15 CFM through the meda. The operating speed of the motor was continually adjustable to provide from 0 to 15 CFM flow while circulating the glovebox atmosphere through the media. Other motors capable of delivering higher flow rates may also be used.

Figure 3:
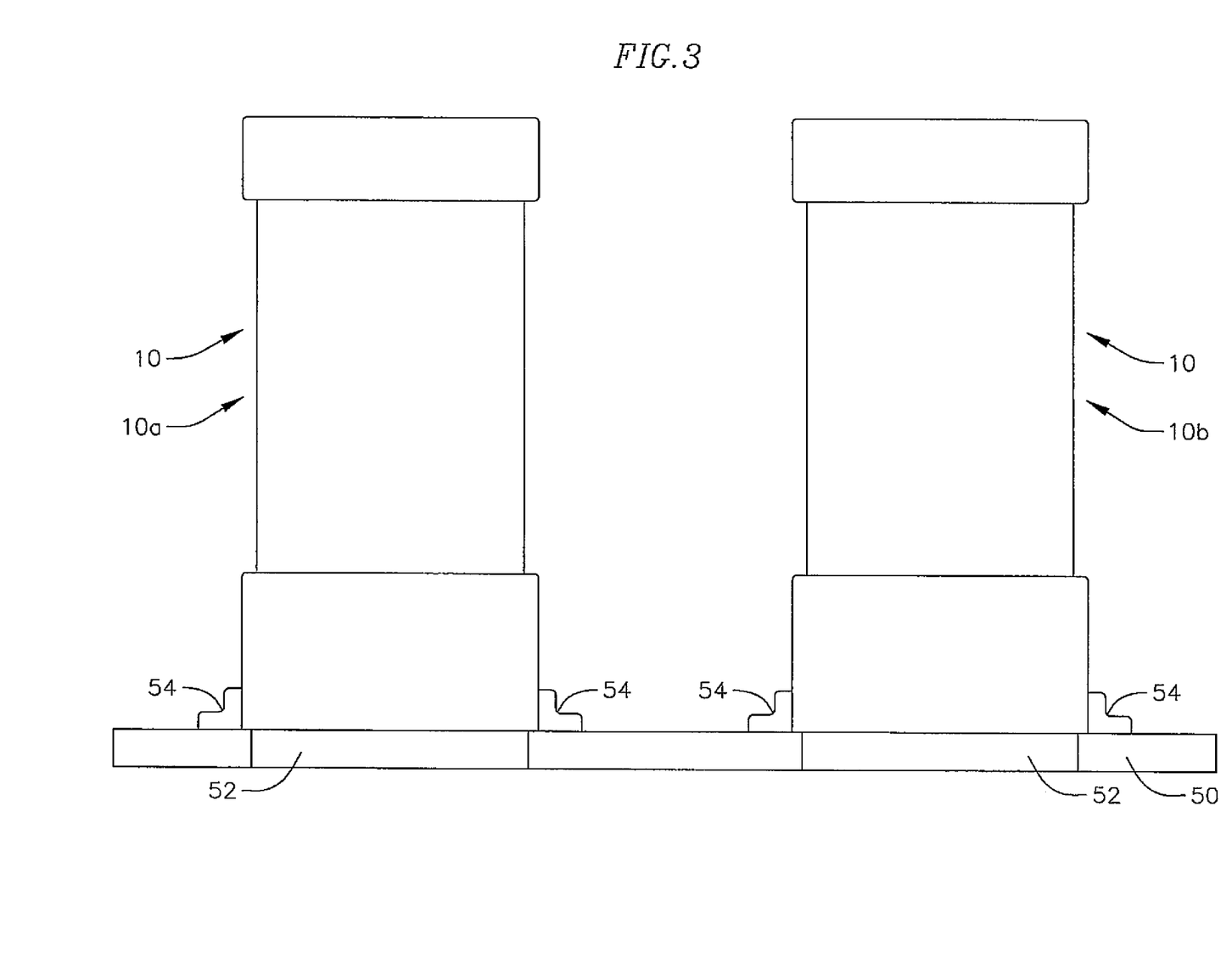
FIG. 3 is a front-view of two apparatuses mounted on a shelf within a glovebox.

In an example embodiment, the example embodiment apparatus is entirely contained within the glovebox. The example embodiment apparatus may be mounted anywhere in the glovebox. In an example embodiment, the apparatus may be mounted on a shelf 50 in the glovebox which has an opening 52 aligned with the open lower end 54 of the apparatus such that the glovebox inert gas atmosphere may flow through the shelf and the apparatus as for example shown in FIG. 3. In an example embodiment, the apparatus is secured to the shelf using clips 54 which are fastened or otherwise attached to the apparatus and the shelf. Other methods of attaching the apparatus to the shelf or any other location on the glovebox may also be used. In another embodiment, the shelf or other supporting surface may not have an opening 52. In such an embodiment, or in other embodiments, the apparatus may be mounted on a stand so that its bottom is spaced apart from a structure on which it is resting so that the inert atmosphere can access the bottom of the apparatus. In another embodiment, the annular member 42 has legs so as to raise the fan assembly from the shelf or other structure. In one example embodiment as shown in FIG. 4, the annular member 42 may be provided with legs 43 forming a base 51 so as to space apart the annular member 42 from a shelf or floor of the glovebox, thus providing atmosphere access to a lower end of the fan assembly.

Figure 5:
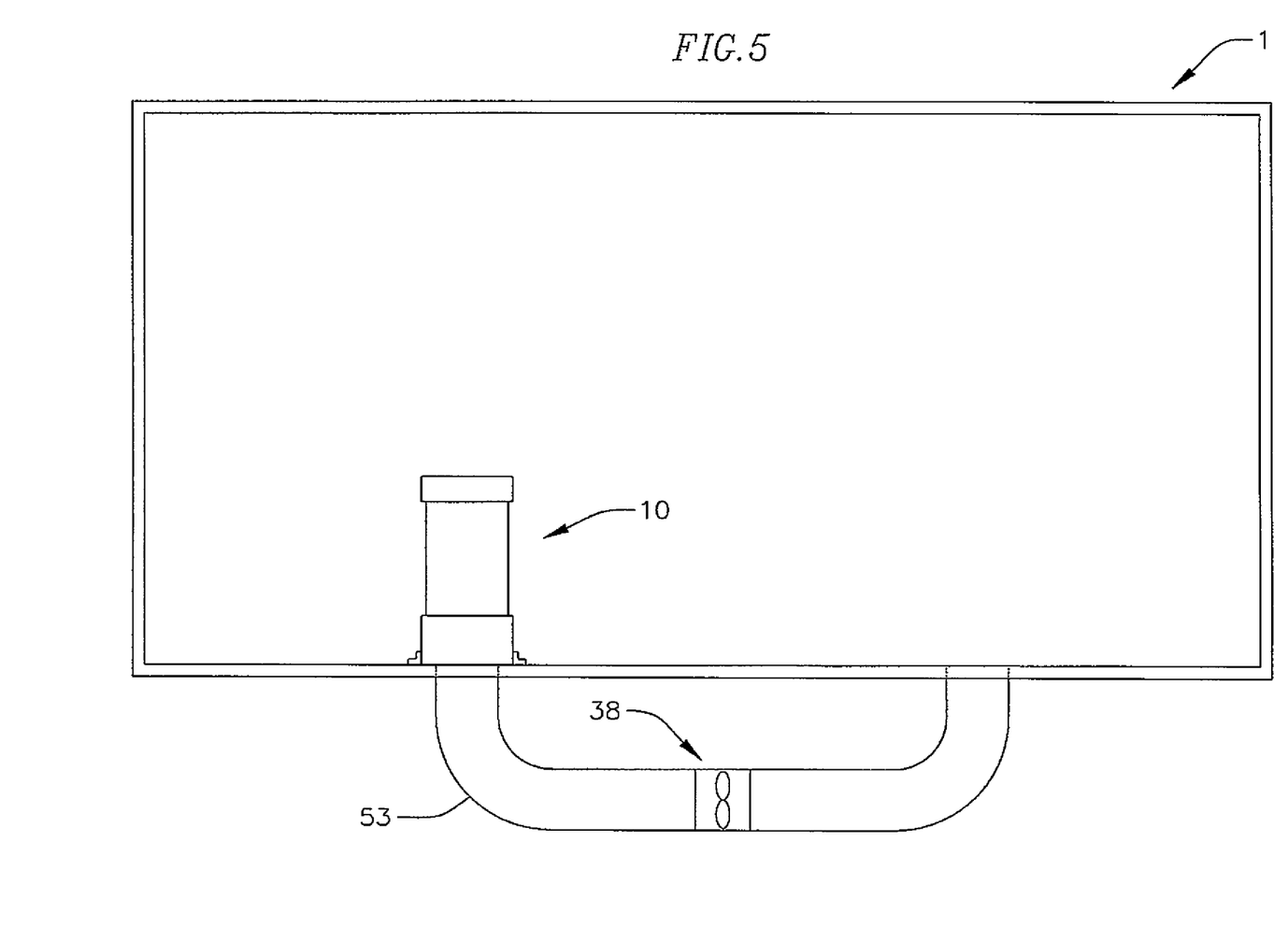
FIG. 5 is a schematic view of a motor with fan mounted externally of the glovebox in a hermetically sealed housing.

In example embodiments the motor with or without the fan may be mounted in an external hermetically sealed housing that is plumbed to the glovebox. This may be desirable when the motor with or without the fan are large and would occupy too much volume if located in the glovebox. For example, the motor with fan 38 may be housed externally of the glovebox 1 in a hermetically sealed tubing 53 that is plumbed through the glovebox to the filtering apparatus 10 for circulating the inert atmosphere through the filtering apparatus 10, as for example shown in FIG. 5. In other example embodiments, a single fan may be plumbed to multiple filtering apparatuses 10 in the glovebox. In other example embodiments, a single motor may be used to drive one or more fans for circulating the inert atmosphere through one or more filtering apparatuses.

Figure 4:
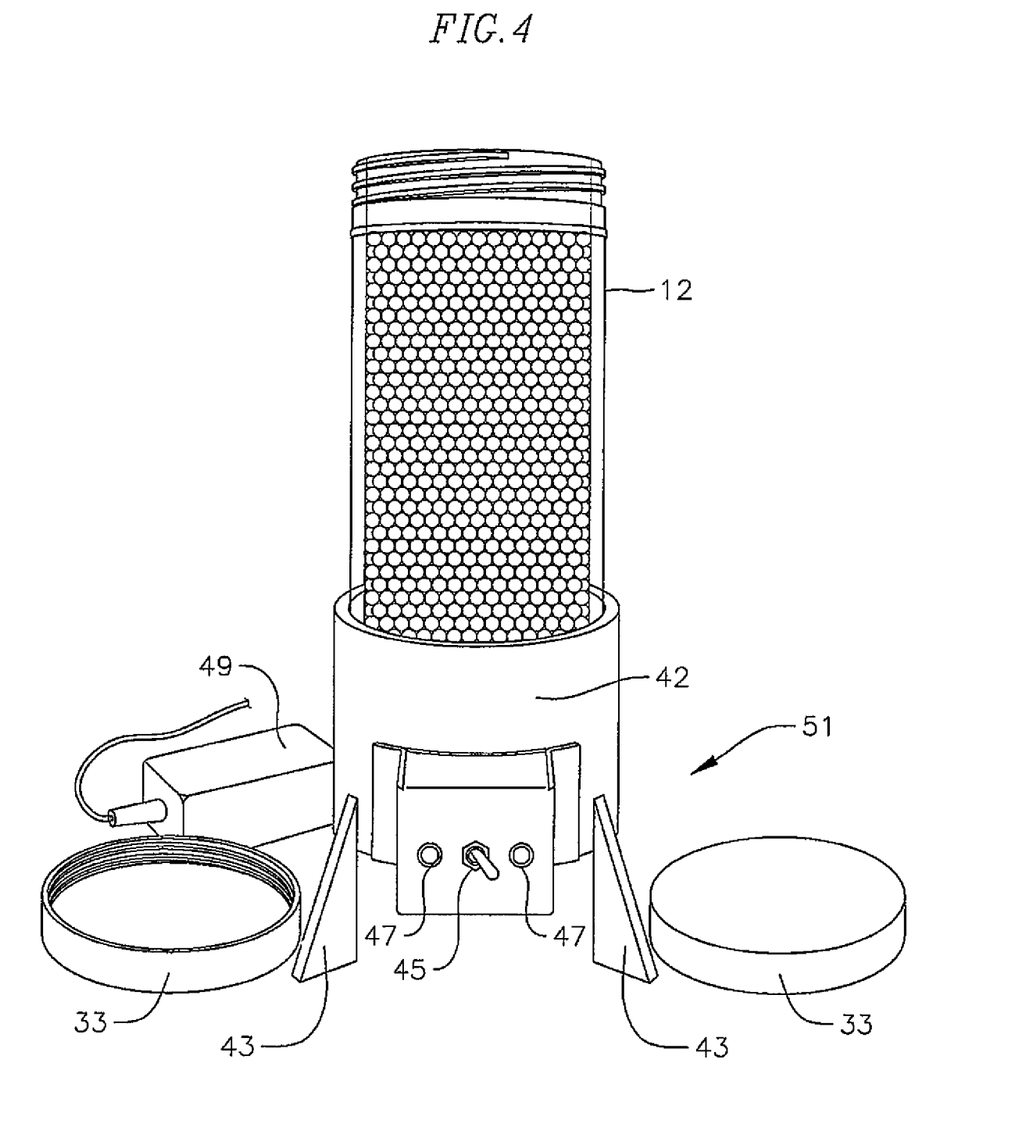
FIG. 4 is a front view of another example embodiment apparatus.

In the example embodiment, as shown in FIG. 4, the fan assembly includes a "HI OFF LO" switch 45 and LED lights 47 and indication fan speed and a 12.0 VDC connector 49 on the rear wall for the connection of a modular power supply or other 12.0 VDC source. The base 51 can be placed anywhere within the glovebox and the body with the desired media can simply be inserted into the base unit. In an embodiment, the body is just rested in the base or fan assembly. In an example embodiment, both moisture removing media, as well as oxygen removing media, may be placed in a single apparatus. In an example embodiment, about 500 gms of an oxygen removal medium and about 500 gms of a moisture removal media is used in the apparatus. In one example embodiment, the two media are mixed. In other example embodiments, one layer of one media is placed over another layer of the other media. In another embodiment, only one apparatus is used having media for either oxygen removal or moisture removal. In yet a further example embodiment, two apparatuses 10a, 10b may be used, one containing media for oxygen removal and the other containing media for moisture removal, as for example shown in FIG. 3. In other example embodiments multiple apparatuses may be placed within the glovebox for either moisture and/or oxygen removal. Media for moisture removal is typically molecular sieve, activated carbon and silica gel desiccants. Media for oxygen removal is copper catalyst. Other materials may also be used for either moisture or oxygen removal. New media in an example embodiment is provided in a sealed container.

The media is placed in the glovebox using known methods to minimize or prevent contamination of the inert atmosphere within the glovebox from the external environment. Once in the glovebox, the cap 30, if used, is removed from the tubular body and the sealed container is opened and the media poured in tubular body over the perforated support member. In another example embodiment, the media may be provided in the container within a perforated material such as for example a mesh. In an example embodiment, the mesh has perforation of a size sufficient for preventing the media particles from penetrating such mesh. With such an embodiment, the mesh containing the media is placed over the perforated support member. With this embodiment, the perforated support member can have perforations that are larger than the particulate size of the media. In such embodiment, the perforated support member may not also be necessary. Moreover, with such an embodiment, a lip, a bar or multiple bars or lips or other structure that may support the mesh with the media may be provided in the apparatus instead of the perforated support member.

In example embodiment, the sealed container is taken in the glovebox, along with an empty container. The used media may be removed from the apparatus and placed in the empty container. The sealed container is unsealed and the media from the opened container is placed in the tubular body over the perforated support member (or other support members). The media that is removed from the glovebox may then be regenerated, activated and sealed in a container offsite and provided to an end user for storage until it needs to be used as a replacement media in the apparatus 10 in a glovebox. To remove the media from the container, the upper end of the apparatus may be removed, as for example, the upper cap (if one is provided) may be unthreaded and the apparatus may be tilted so as to remove the media. In another example embodiment, the tubular body 12 may be disconnected (as for example it may be unthreaded if previously threaded) from the fan assembly.

Figure 6:
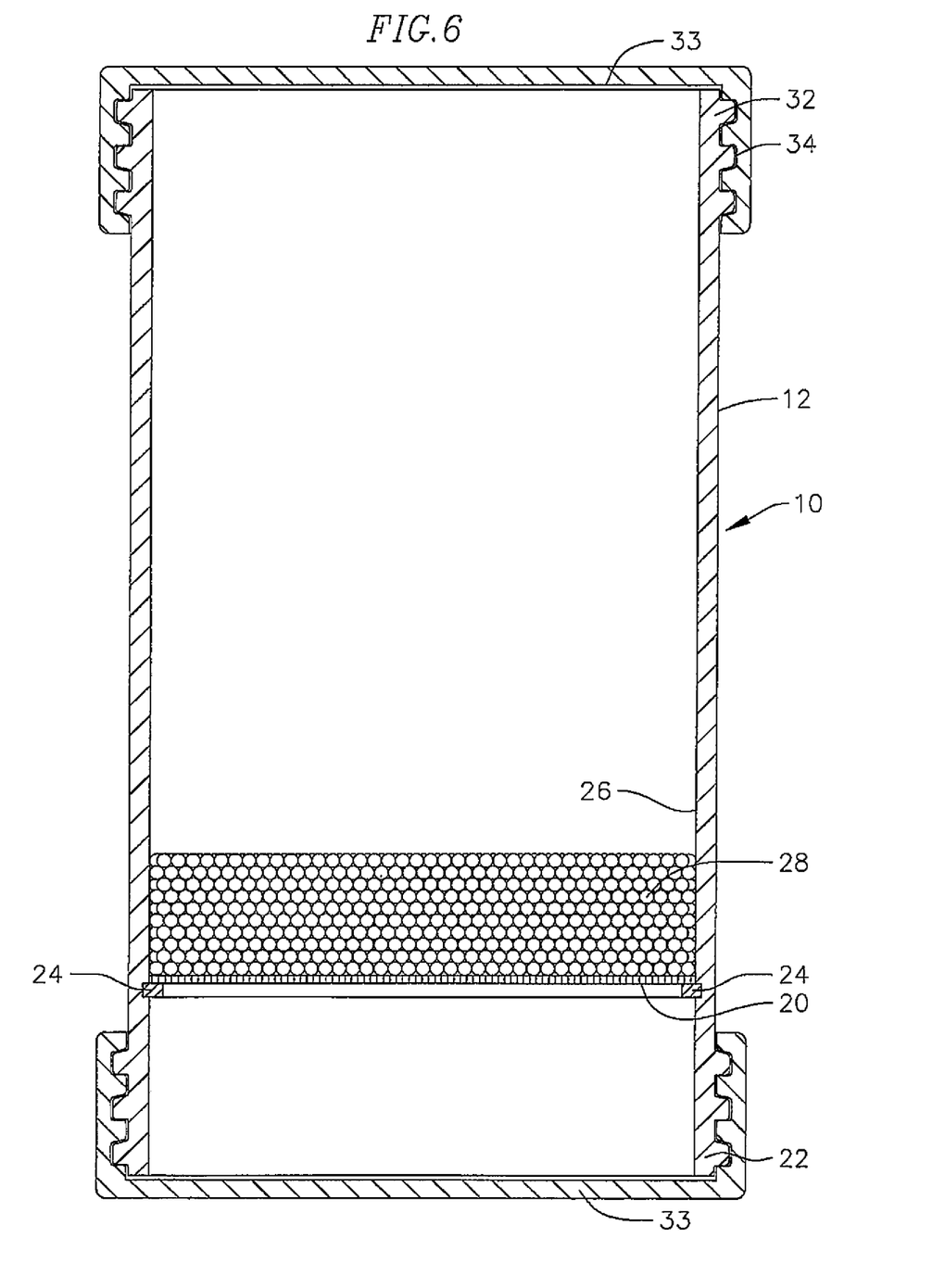
FIG. 6 is a cross-sectional view of an example embodiment filtering capsule.

In another example embodiment, the container may form a portion of the apparatus. For example the container may be the tubular body 12 (FIG. 2). In such embodiment, the container may be provided including the media and may include capped ends, as for example shown in FIG. 6. Such container including said media may be referred to herein for convenience as a "filtering capsule." The ends may be capped with threaded caps 33, as for example shown in FIG. 6, or other means as for example a lid or film or other material attached to the upper and lower end of the body (i.e., the container) for sealing such ends. Once in the glovebox, the body is uncapped and threaded onto the fan assembly. In yet another example embodiment, the entire apparatus with the media including the fan assembly is the container. In such an embodiment, the entire apparatus is replaced when replacing of the media is required. In other example embodiment, the body including the filtering media may be provided ready to be installed in line with the fan at an appropriate location within the glovebox. In this regard, when the filtering media needs to be replaced, the body of the filtering apparatus with the spent filtering media is replaced with another body with the new filtering media. The old body with the spent filtering media may be sent to an appropriate source where the filtering media may be regenerated and thus, be ready for re-use.

In use, the motor operates to rotate the fan causing the inert atmosphere within the glovebox to continuously flow through the apparatus and the media. The inert atmosphere within the glovebox is thus continuously circulated through the media thereby having the moisture and/or oxygen levels in such circulated air reduced or maintained at a desired level, as for example a level less than 1 ppm.

In example embodiment, the system uses full motor speed or a speed for producing a flow rate of approximately 5 CFM to rapidly reduce the glovebox oxygen level from 200 ppm to less than 1 ppm. Applicant has discovered that a fresh bed of the oxygen removal media in the apparatus will reduce the oxygen ($O_2$) level in a typical glovebox single work station having one pair 0.030 inch gloves from 200 ppm to 1 ppm in less than one hour. In an example embodiment, once the level of oxygen in the glovebox has been reduced to less than 1 ppm, the motor may be reduced to half speed to maintain about 3 CFM flow which is sufficient for maintaining an oxygen level of 1 ppm in the glovebox and for overcoming any oxygen diffusion through the gloves. Applicant has discovered that an example apparatus will maintain the glovebox at less than 1 ppm for weeks, or months. As soon as air enters the glovebox and the oxygen level increases beyond 200 ppm, the fan motor is turned off and the glovebox atmosphere is purged with inert gas from an inert gas supply until the oxygen level in the glovebox is less than 200 ppm. Once the 200 ppm level is reached, the purged operation is stopped and the fan motor is turned on to full speed position for maximum flow through the removal media. The apparatus then reduces the oxygen level to less than 1 ppm. If the recovery time becomes too long, the user should replace the oxygen removal media with fresh oxygen removal media. If the oxygen level is reduced to less than 1 ppm and the system is not capable of maintaining the oxygen level at less than 1 ppm, that may be a good indicator that the media needs replacing.

With the apparatus disclosed herein expensive mixed regeneration gas is not by the user required to regenerate the media used by the glovebox, and only a few minutes are required to replace the exhausted media. In an example embodiment, the apparatus may be located within the glovebox in a movable fixture or in a fixture built into a glovebox. In an example embodiment, the media is provided to the glovebox user fully regenerated and sealed within a container. In the example embodiment where the media is provided in a container such as a tubular container or the tubular body forming part of the apparatus, the tubular container or body with lids or caps on both ends of the cylinder is brought into the glovebox through the glovebox antechamber. The old tubular container or body is removed from the fan assembly, the lids are then removed from the new tubular container or body, and the new tubular container or body is connected to the fan assembly.

Containers or bodies of regenerated media can be stored near the glovebox for immediate use thus eliminating the need for storing expensive mixed gases and the user does not have to wait 12 or more hours to regain use of the glovebox following the typical prior art regeneration process. Thus, no regeneration gas is required to be provided by the glovebox user and no long regeneration process at the glovebox is required and the glovebox is only out of service for a few minutes. The example embodiment apparatus allows gloveboxes to be used in areas where reliable media regeneration sources are not available.

In example embodiments, the filtering apparatus may be used to remove any oxygen and/or water vapor and/or solvent vapor and/or nitrogen from an inert atmosphere inside the glovebox. The inert atmosphere may be nitrogen, argon, neon, helium, or any combination thereof and may include air. In other example embodiments, the filtering apparatus may be used to remove nitrogen from argon or helium or from a mixture of these gases. In an example embodiment, for oxygen removal, a copper catalyst filtering media may be used which captures unwanted oxygen molecules. For water or solvent removal, the filtering media may be any of a molecular sieve, activated carbon, or silica gel desiccants or any combination thereof which capture unwanted water or solvent molecules by adsorption. For nitrogen removal activated carbon may be used as the filtering media. In other example embodiments, the filtering apparatus may be used to remove various contaminants from the inert atmosphere using appropriate media. In an example embodiment, a filtering apparatus may include more than one filtering media. In this regard a single filtering apparatus may be used, to remove water, solvent, oxygen and/or nitrogen. In example embodiments, the different types of filtering media may be mixed together or may be provided is adjacent or spaced apart layers, with each layer being a different filtering media. In alternate example embodiments, separate filtering apparatus may be used to remove each different type of contaminant. In example embodiment, removal of contaminants using the example embodiment filtering apparatus occurs at room temperature.

Although relative terms such as "outer," "inner," "upper," "lower," "below," "above," "vertical, "horizontal" and similar terms may have been used herein to describe a spatial relationship of one element to another, it is understood that these terms are intended to encompass different orientations of the various elements and components of the device in addition to the orientation depicted in the figures. For example, an upper element may be below a lower element.

Although only a few example embodiments have been described in detail above, those skilled in the art will readily appreciate that many modifications are possible in the example embodiments without materially departing from this invention. For example, in other embodiments, instead of a cap, an upper perforated member is attached to an upper end of the body 12. The upper perforated member may be attached using any method. For example it may be clamped to an outer surface of the body or it may be adhered to the body. In another example embodiment, the apparatus 10 does not include a cap 30 or an upper perforated member such that the upper end of the body 12 remains open. In other embodiments, the fan may draw the atmosphere through the media, or push the atmosphere through the media. Accordingly, all such modifications are intended to be included within the scope of this disclosure as defined in the following claims. It is the express intention of the applicant not to invoke 35 U.S.C. 112, paragraph 6 for any limitations of any of the claims herein, except for those in which the claim expressly uses the words 'means for' together with an associated function.

What is claimed is:

1. An apparatus for the removal of at least one contaminant from an inert atmosphere in a glovebox, the apparatus comprising:
   a body having a size allowing for insertion into said glovebox comprising at least one of an acrylic, polycarbonate, or PVC;
   a media comprising a copper catalyst in the body for the removal of at least one of said contaminant from said inert-atmosphere flowing through said media;
   a fan in a housing for causing said inert atmosphere to flow through said body and media, wherein the housing is coupled to the body; and
   a motor for driving said fan.

2. The apparatus as recited in claim 1, wherein said at least one contaminant is selected from the group consisting essentially of moisture, oxygen, solvent and combinations thereof.

3. The apparatus as recited in claim 1, wherein the inert atmosphere is an atmosphere selected from the group consisting essentially of nitrogen, argon, neon, helium, combinations thereof, and air combined with either of the aforementioned atmospheres.

4. A glovebox with a purification apparatus combination comprising:
   a glovebox having an interior space;
   a purification apparatus within said interior space for the removal of at least one contaminant from an inert atmosphere within said interior space, said purification apparatus comprising,
      a body comprising at least one of an acrylic, polycarbonate, or PVC,
      a media comprising a copper catalyst in the body for the removal of at least one contaminant from said inert atmosphere flowing through said media and body,
      a fan in a housing for causing said inert atmosphere to flow through said body and media, wherein the housing is coupled to the body, and
      a motor for driving said fan.

5. The combination as recited in claim 4, further comprising another purification apparatus comprising;
   another body comprising at least one of an acrylic, polycarbonate, or PVC;
   another media in said another body for the removal of at least one of said moisture and oxygen from an atmosphere flowing through said another media;

another fan in another housing for causing the atmosphere to flow through said another body and said another media, wherein said another housing is coupled to said another body; and another motor for driving said another fan.

6. The combination as recited in claim 5, wherein said media in said purification apparatus body is a media for removing moisture and said another media is said another purification apparatus another body is for removing oxygen.

7. The combination as recited in claim 4, wherein said at least one contaminant is selected from the group consisting essentially of moisture, oxygen, solvent and combinations thereof.

8. The combination as recited in claim 4, wherein the inert atmosphere is an atmosphere selected from the group consisting essentially of nitrogen, argon, neon, helium, combinations thereof, and air combined with either of the aforementioned atmospheres.

9. A glovebox with a purification apparatus combination comprising:

a glovebox having an interior space;

an apparatus within said interior space for the removal of at least one contaminant from an inert atmosphere within said interior space, said apparatus comprising,
 a body comprising at least one of an acrylic, polycarbonate, or PVC, and
 a media comprising a copper catalyst in the body for the removal of at least one contaminant from said inert atmosphere flowing through said body and media;
a fan in a housing for causing said inert atmosphere to flow through said body and media, wherein the housing is coupled to the body, and
a motor externally of the glovebox for driving said fan.

10. The combination as recited in claim 9, wherein said at least one contaminant is selected from the group consisting essentially of moisture, oxygen, solvent and combinations thereof.

11. The combination as recited in claim 9, wherein the inert atmosphere is an atmosphere selected from the group consisting essentially of nitrogen, argon, neon, helium, combinations thereof, and air combined with either of the aforementioned atmospheres.

* * * * *

UNITED STATES PATENT AND TRADEMARK OFFICE
CERTIFICATE OF CORRECTION

PATENT NO. : 10,549,004 B2
APPLICATION NO. : 14/315216
DATED : February 4, 2020
INVENTOR(S) : Melvin W. Hughes et al.

It is certified that error appears in the above-identified patent and that said Letters Patent is hereby corrected as shown below:

In the Claims

Column 11, Line 7, Claim 6   delete "media in said purification apparatus body is a media" and insert -- another media in said another body is --

Column 11, Line 8, Claim 6   delete "another media is said another" and insert -- media in said --

Column 11, Line 9, Claim 6   after "purification" delete "apparatus another"

Signed and Sealed this
Twelfth Day of January, 2021

Andrei Iancu
*Director of the United States Patent and Trademark Office*